US011304933B2

(12) United States Patent
Lee et al.

(10) Patent No.: US 11,304,933 B2
(45) Date of Patent: *Apr. 19, 2022

(54) FAST ACTING ORALLY DISINTEGRATING FILM

(71) Applicant: TAHO Pharmaceuticals Ltd., Taipei (TW)

(72) Inventors: Catherine Lee, Happy Valley, OR (US); Chien-Chiao Wang, New Taipei (TW)

(73) Assignee: TAHO PHARMACEUTICALS LTD., Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 16/569,979

(22) Filed: Sep. 13, 2019

(65) Prior Publication Data

US 2020/0000773 A1 Jan. 2, 2020

Related U.S. Application Data

(63) Continuation of application No. 15/351,368, filed on Nov. 14, 2016, now Pat. No. 10,456,378, which is a continuation of application No. PCT/US2015/037045, filed on Jun. 23, 2015.

(51) Int. Cl.
| | |
|---|---|
| A61K 31/4178 | (2006.01) |
| A61K 9/00 | (2006.01) |
| A61K 47/38 | (2006.01) |
| A61K 47/26 | (2006.01) |
| A61K 47/36 | (2006.01) |
| A61K 9/70 | (2006.01) |
| A61K 47/10 | (2017.01) |
| A61K 47/32 | (2006.01) |

(52) U.S. Cl.
CPC ........ *A61K 31/4178* (2013.01); *A61K 9/0056* (2013.01); *A61K 9/7007* (2013.01); *A61K 47/10* (2013.01); *A61K 47/26* (2013.01); *A61K 47/32* (2013.01); *A61K 47/36* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 7,390,503 | B1 | 6/2008 | Ahmed et al. |
| 7,666,337 | B2 | 2/2010 | Yang et al. |
| 8,580,830 | B2 | 11/2013 | Leichs et al. |
| 8,623,826 | B2 | 1/2014 | Trento et al. |
| 8,715,715 | B2 | 5/2014 | Ryoo et al. |
| 8,771,736 | B2 | 7/2014 | Ryoo et al. |
| 8,900,634 | B2 | 12/2014 | Ryoo et al. |
| 9,492,379 | B2 | 11/2016 | Park et al. |
| 9,682,037 | B2 | 6/2017 | Leichs et al. |
| 9,884,014 | B2 | 2/2018 | Venkatesh |
| 2005/0147653 | A1 | 7/2005 | Yasuda et al. |
| 2006/0078614 | A1 | 4/2006 | Venkatesh |
| 2008/0131467 | A1 | 6/2008 | Nelson et al. |
| 2010/0297232 | A1 | 11/2010 | Myers et al. |
| 2011/0237563 | A1 | 3/2011 | Costantini |
| 2011/0160264 | A1 | 6/2011 | Myers et al. |
| 2011/0182969 | A1 | 7/2011 | Yang et al. |
| 2012/0064153 | A1 | 3/2012 | Trento et al. |
| 2013/0059854 | A1 | 3/2013 | Ryoo et al. |
| 2014/0073678 | A1 | 3/2014 | Dadey et al. |

FOREIGN PATENT DOCUMENTS

| | | |
|---|---|---|
| EP | 2253224 A1 | 11/2010 |
| EP | 2431028 A2 | 3/2012 |
| WO | 03086361 A1 | 10/2003 |
| WO | 2012053006 A2 | 4/2012 |
| WO | 2013015545 A1 | 1/2013 |

OTHER PUBLICATIONS

Jani et al (Pharma Science Monitor 3(4) Suppl-1:2463-2476, 2012) (Year: 2012).*
Nagar et al (Drug Invention Today 3(12):280-289, 2011) (Year: 2011).*
Borges et al. "Oral Films: Current Status and Future Perspectives II." Mar. 14, 2015. Journal of Controlled Release 206(2015) 108-121. Elsevier B.V. Amsterdam, Netherlands.
Coppens et al. "Thermal and Rheological Evaluation of Pharmaceutical Excipients for Hot Melt Extrusion." AAPS Annual Meeting and Exposition, Baltimore, MD. Nov. 7-9, 2004.
Extended European Search Report in corresopnding European Patent Application No. 15811604.6 dated Jan. 23, 2018.
Hirpara et al. "Optimization & Screening of Different Film Forming Polymers and Plasticizers In Fast Dissolving Sublingual Film." International Journal of Pharmacy and Pharmaceutical Sciences, vol. 6, Issue 6, 2014, ISSN-0975-1491.

(Continued)

*Primary Examiner* — Craig D Ricci
(74) *Attorney, Agent, or Firm* — Leason Ellis LLP (57) ABSTRACT

A fast acting orally disintegrating film (ODF) for treatment of various medical conditions including emesis that has a simple formulation, easy to manufacture and has similar pharmacokinetic profile to currently commercially available orally administered drug products is provided. The ODF comprises an active pharmaceutical ingredient such as ondansetron or a pharmaceutical acceptable salt thereof in an amount of 2 to 24 mg, at least one hydrophilic film forming polymer in an amount of at least 8% by weight of the film, wherein the at least one hydrophilic film forming polymer is characterized by having a molecular weight of 5000 to 50000 Da, and a water soluble excipient in an amount of 10 to 30% by weight of the film. The present invention also provides a method for preparing the ODF that remains stable over a period of time under a normal pharmacologically storage condition and a method for treating or preventing various medical conditions such as nausea or vomiting or a treatment method mediated through antagonizing action of 5HT at 5-HT3 receptor by administering the ODF to a patient in need thereof.

12 Claims, 7 Drawing Sheets

(56) References Cited

OTHER PUBLICATIONS

Jani et al. "Formulation and Evaluation of Fast Releasing Film of Ondansetron Hydrochloride." Pharma Science Monitor, vol. 3, Issue-4, Suppl-1, Nov. 2012 ISSN: 0976-7908.

Kalyan et al. "Recent Trends in the Development of Oral Dissolving Film." Apr. 2012. Intl J PharmTech Res vol. 4 No. 2:725-733, Sphinx. India.

Keshavarao et al. "Formulation and Evaluation of Mouth Dissolving Film Containing Rofecoxib." 10/0312011. IRJ P 2(3) 2011 :273-278. India.

Koland et al. "Fast Dissolving Sublingual Films ofOndansetron HC1." J Young Pharm. Jul.-Sep. 2010. Elsevier, NL https://www.ncbi.nlm.nih.gov/pmc/articles/PMC2964757.

Kumria et al. "Oral buccoadhesive films of ondansetron: Development and evaluation." International Journal of Pharmaceutical Investigation 3.2 (2013): 112.

Mishra et al. "Formulation and Character of Rapidly Dissolving Films." IndJ Pharm Ed Res. Jan.-Mar. 2011 vol. 45 71 77. Ass. Pharm. Teachers of India. India. Aug. 8, 2010.

Nagar et al. "Formulation and Evaluation of Mouth Dissolving Film of Antipsychotic Drug Aripiprazole." Der Pharmacia Lettre, 2012, 4(4):1221-1227. Scholar Research Library. India.

No Author. "Using Dow Excipients for Controlled Release of Drugs in Hydrophilic Matrix Systems." The Dow Chemical Company. Published Jul. 2000. 3 pages.

No Author. "Using Dow Excipients for Controlled Release of Drugs in Hydrophilic Matrix Systems." The Dow Chemical Company. Sep. 2006. 36 pages.

Patel et al. "Formulation Development and Evaluation of Mouth Melting Film of Ondansetron." Arch Pharm Sci & Res vol. 1 No. 2 212-217 Oct. 2009.

Prabhu et al. "Formulation and Evalulation of Fast Dissolving Films of Levocitirizine Di HCI." Apr. 2011. Intl J Pharm Inves. vol. 1 Issue 2: 99-104. JPI India.

Siddiqui et al. "A Short Review on a Novel Approach in Oral Fast Dissolving Drug Delivery System and Their Patents." 2011 Adv in Bio Res 5(6):291-303. IDOSI India.

Written Opinion in corresponding Singapore Patent Application No. 11201610358X dated Jan. 8, 2018.

* cited by examiner

FAST ACTING ORALLY DISINTEGRATING FILM

CROSS-REFERENCE TO RELATED APPLICATION(S)

The present application is a continuation application of U.S. patent Ser. No. 15/351,368 filed on Nov. 14, 2016, entitled FAST ACTING ORALLY DISINTEGRATING FILM, which was a continuation of PCT/US15/37045 filed on Jun. 23, 2015, entitled "FAST ACTING ORALLY DISINTEGRATING FILM," which, in turn, claims priority to U.S. Provisional Application No. 62/016,643, filed on Jun. 24, 2014, entitled "FAST ACTING ORALLY DISINTEGRATING FILM WITH ONDANSETRON AS ACTIVE PHARMACEUTICAL INGREDIENT" all of which are incorporated by reference in their entireties.

FIELD OF THE INVENTION

The present invention relates to an orally disintegrating film for administration of drugs and a method for preparing the orally disintegrating film. In particular, the invention relates to a fast acting orally disintegrating film (ODF), a method for preparing the fast acting ODF and a method for administration of drugs using the ODF of the present invention.

BACKGROUND OF THE INVENTION

There exist various ways of administering drugs. They include oral tablets, orally disintegrating tablets, oral solution and injectables. However, aside from injectable form, which is invasive, the other administration routes may not be suitable for those patients who have difficulty swallowing, such as children and the elderly as well as people with buccal conditions. Instead, a more appropriate administration route for patients who have difficulty swallowing may be orally disintegrating film (ODF), which has recently been developed for the pharmaceutical industry and can be adapted for a plethora of popular drugs such as ondansetron. Due to its ease of handling and storage as well as the fact that it does not require swallowing solids such as tablets, administration of drugs via ODF is beneficial, especially for those who have difficulty swallowing.

An ODF typically has an established shelf-life of 2-3 years, depending on the active agent. However, it can be extremely sensitive to environmental moisture (Siddiqui et al., *Advan. Biol. Res.*, 5(6): 291-303, 2011) as well as other environmental influences such as temperature and pH under various storage conditions. Therefore, functional excipients such as stabilizer (stabilizing agents), disintegrants, solubizer and filming-forming agents (in contrast to non-functional excipients such as sweetners, flavoring agents, etc. . . . ), have been described in other ODFs to enhance the ODF quality and performance properties.

As an illustration, there are various patents that describe application of ODF technology to ondansetron with functional excipients as additives. For example, U.S. Pat. No. 8,580,830, to Leichs et al., discloses adding pH adjusting agents to enhance ondansetron stability and to stimulate saliva for dissolving the film.

In addition, U.S. Pat. No. 8,663,687, to Myers et al. proposes preparing film compositions for delivery of drugs by including polyethylene oxide and saccharide-based polymer as a water soluble polymer composition in order to resolve any air trapping and void formation problems associated with conventional film forming process. The patent further claims incorporating active agents into nanoparticles or microparticles so as to ensure a non-self aggregating uniform heterogeneity.

Further, U.S. Pat. No. 8,658,201, to Singh et al., discloses a rapidly dissolving film having significant drug loading capability while providing sustained and controlled release of an active agent. This film is made up of high molecular weight hydrophilic polymers in combination with a rapidly dissolving polymeric material including water soluble sugars, semi-synthetic and synthetic polymers, and commercially available disintegrants.

Rather than using additives and complex formulations by the use of functional excipients as described in the patent listed above, there is a need for a fast acting ODF with a formulation that is easy to manufacture into a product and avoids a substantial number of additives that heretofore have been seen in many other ODF products while, at the same time, achieves desirable characteristics in an ODF product such as short buccal disintegration times, short dissolution times, strength for withstanding handling, minimum of gas bubbles, uniform distribution of API, smooth appearance appropriate for commercialization, etc . . . .

SUMMARY OF THE INVENTION

Accordingly, it is one objective of the present invention to provide a fast acting ODF for treatment of emesis.

The present invention provides a fast acting disintegrating film which comprises ondansetron or a pharmaceutical acceptable salt thereof in an amount of 2 to 24 mg, at least a first hydrophilic film forming polymer in an amount of at least 8% by weight of the film, wherein the first hydrophilic film forming polymer is characterized by having a molecular weight of 5000 to 50000 Da and viscosity of 3 to 10 cps, and a water soluble excipient in an amount of 10 to 30% by weight of the film.

The fast acting integrating film further comprises a second hydrophilic film forming polymer characterized by having a molecular weight of equal or greater than 50000 Da and viscosity equal or greater than 15 cps, wherein said first hydrophilic film forming polymer is mixed with said second hydrophilic film forming polymer in a ratio of at least about 0.1:1. In some embodiments, the mixture of said first hydrophilic film forming polymer to said second hydrophilic film forming polymer may be at a ratio of more than 0.5:1. And in other embodiments, the first hydrophilic film forming polymer may be in an amount of more than 20%, 50% or 65% by weight of the film.

Another object of the present invention is to provide a method for preparing the ODF that remains stable over a period of time under a normal pharmacologically storage condition.

Therefore, a method for preparing an orally administrable film dosage form is provided. The preparation method involves dissolving in water a pharmaceutically acceptable amount of active pharmaceutical ingredient, at least one hydrophilic film forming polymer in an amount of at least 8% by weight of the dosage form and is characterized by having a molecular weight of 5000 to 50000 Da and viscosity of 3 to 10 cps, and a water-soluble excipient in an amount of 10 to 30% by weight of the dosage form to form a viscous solution with a measured viscosity of about 2000 to 10000 cps. A layer of the viscous solution is then coated on a casting film and dried in an oven at about 8G ° C. over a period of about 20 minutes so as to form the orally administrable film of desired thickness and size.

In alternative embodiments, the method may further involves mixing another hydrophilic film forming polymer characterized by having a molecular weight of equal or greater than 50000 Da, wherein said at least one hydrophilic film forming polymer is mixed with said another hydrophilic film forming polymer in a ratio of at least about 0.1:1. And according to certain embodiments, said at least one hydrophilic film forming polymer may be mixed with said another hydrophilic film forming polymer at a ratio of more than 0.5:1.

Still another object of the present invention is to provide an orally administered film that can disintegrate upon contact of saliva in the buccal cavity within about sixty seconds.

The present invention provides an orally administered film characterized by having a pre-drying solution blend with a measured viscosity of about 2000 to 10000 cps. The orally administered film comprises ondansetron or pharmaceutical acceptable salt thereof in an amount of about 4 to 8 mg, at least one hydrophilic film forming polymer in an amount of at least 8% by weight of the film, wherein the at least one hydrophilic film forming polymer is characterized by having a molecular weight of 5000 to 50000 Da, and a water soluble excipient in an amount of 10 to 30% by weight of the film.

Optionally, the orally administered film or fast acting orally disintegrating film may further include other ingredients such as one or more flavoring agent, sweetening agent and coloring agent to be dissolved or mixed with the pharmacologically active agent, hydrophilic film forming polymers and water soluble excipients in the method for preparing the film.

Yet another object of the present invention is to provide a method for treating emesis using the ODF that mediates through antagonizing the action of 5-hydroxytryptamine (5HT or serotonin) at 5-HT3 receptors.

The present invention also provides a method for treating or preventing nausea or vomiting or a treatment method mediated through antagonizing action of 5HT at 5-HT3 receptor by administering the above mentioned fast acting orally disintegrating film or orally administered film to a patient in need thereof.

BRIEF DESCRIPTION OF THE DRAWINGS

Tables 1 provides viscosity and average molecular weight of the hydrophilic film forming polymers used in the present invention.

Tables 2A and 2B list example formulations of the orally disintegrating film (ODF) of the present invention.

Table 3 illustrates stability of the ODF of the present invention by summarizing impurity presence data for the ODFs tested at long term storage conditions and accelerated condition.

Table 4 illustrates stability of formulation 1 of the ODF of the present invention by summarizing a comparison of impurity presence data between the ODFs against Zuplenz 4 mg ondansetron OSF.

Table 5 illustrates the comparison of dissolution data between formulation 1 of the ODF of the present invention against marketed Zuplenz 4 mg ondansetron OSF stressed under 60 degrees Celsius and 60% RH for 0 days, 7 days and 14 days.

Table 6 summarizes comparison of tension forces that may be applied before the formula 1 of the ODF of the present invention would tear as compared against marketed Zuplenz ondansetron OSF.

DETAILED DESCRIPTION OF THE INVENTION

As used in this specification and in claims which follow, the singular forms "a", "an" and "the" include plural referents unless the context clearly indicates otherwise. Thus, for example, reference to "an ingredient" includes mixtures of ingredients, reference to "an active pharmaceutical agent" includes more than one active pharmaceutical agent, and the like.

The terms "active agent", "pharmacologically active agent" and "drug" are used interchangeably herein to refer to a chemical material or compound that includes a desired pharmacological, physiological effect and include agents that are therapeutically effective. The terms also encompass pharmaceutically acceptable, pharmacologically active derivatives and analogs of those active agents specifically mentioned herein, including, but not limited to, salts, esters, amides, prodrugs, active metabolites, inclusion complexes, analogs and the like.

As used herein, the term "about" as a modifier to a quantity is intended to mean + or − 5% inclusive of the quantity being modified.

As used herein, the term "disintegrate", "disintegrating", and "disintegrated" is intended to mean dispersing or otherwise breaking apart into small pieces that are undetectable by the naked eye so that they can be swallowed and processed by the gastrointestinal system.

As used herein, the term "dissolution" is intended to mean disintegration as defined above followed by further breaking down of the small pieces so as to free active pharmaceutical ingredient from the excipient or any other components of the present invention for absorption by the gastrointestinal system.

The term "effective amount" or "a therapeutically effective amount" of a drug or pharmacologically active agent is intended to mean a nontoxic but sufficient amount of the drug or active agent for providing the desired therapeutic effect. The amount that is "effective" will vary from subject to subject, depending on the age and general condition of the individual, the particular active agent or agents, and the like. An appropriate "effective" amount in any individual case may be determined by one of ordinary skill in the art using routine experimentation.

It will be understood that the term "film" comprises thin films and sheets, in any shape, including rectangular, square, or other desired shape. The films described herein may be of any desired thickness and size suitable for the intended use. For example, a film of the present invention may be sized such that it may be placed into the oral cavity of the user. For example, some films may have a relatively thin thickness of from about 10 to about 500 micrometers, while others may have a somewhat thicker thickness of from about 500 to about 10000 micrometers. In addition, the term "film" includes single layer compositions as well as multi-layer compositions, such as laminated films, coatings on films and the like.

The present invention discloses a fast acting ODF made using a formulation that quickly disintegrates in the mouth when exposed to saliva, which is critical for people who have difficulty swallowing. Specifically, film forming polymers of various viscosities and molecular weights can be used in pre-drying mixture solution for making an ODF so that the resulting ODF can have different characteristics based on the type of polymers used. By utilizing film forming polymers of certain ranges of viscosities and molecular weights each at certain ranges of percentage weight of total composition of the ODF, the ODF of the present invention is made to be fast acting as defined by the ODF's capacity to disintegrate quickly when in contact with saliva. The fast acting aspect of the present invention is satisfied if an ODF disintegrates in about thirty seconds or less when placed in about 20 cc of water at about 37 degrees Celsius and lightly shaken. It should be noted that the ODF of the present invention achieves the fast disintegration time without aid of functional excipients such as disintegrants.

Referring to tables 2A and 2B, these tables list various formulations of the ODF of the present invention. All of these formulations are capable of disintegrating in about 30 seconds or less when placed in about 20 cc of water at about 37 degrees Celsius and lightly shaken.

Figure 1:
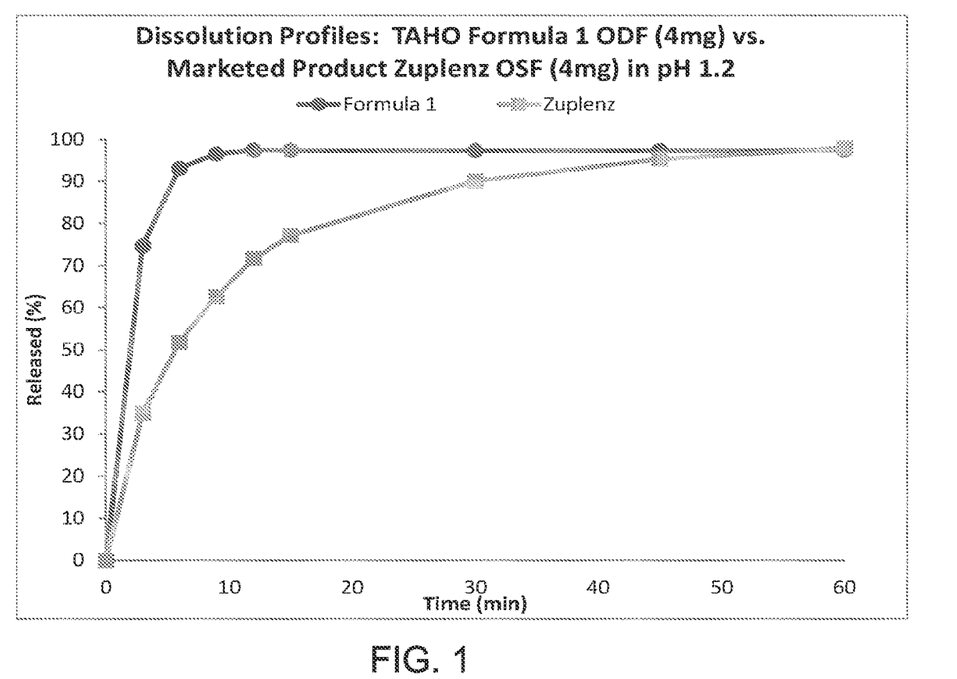
FIG. 1 is a comparison of dissolution profiles of Zuplenz® 4 mg ondansetron oral soluble film (OSF) against formulation 1 of 4 mg ondansetron ODF of the present invention, both dissolved using a dissolution medium at pH 1.2.
Figure 2:
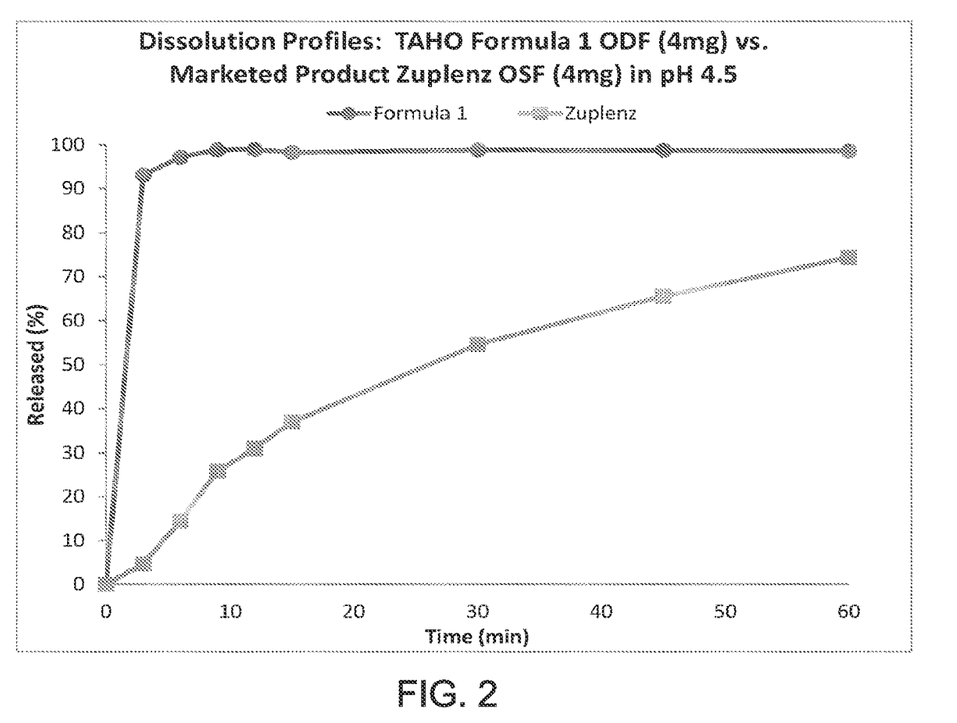
FIG. 2 is a comparison of dissolution profiles of marketed Zuplenz 4 mg ondansetron OSF against formulation 1 of 4 mg ondansetron ODF of the present invention, both dissolved using a dissolution medium at pH 4.5.
Figure 3:
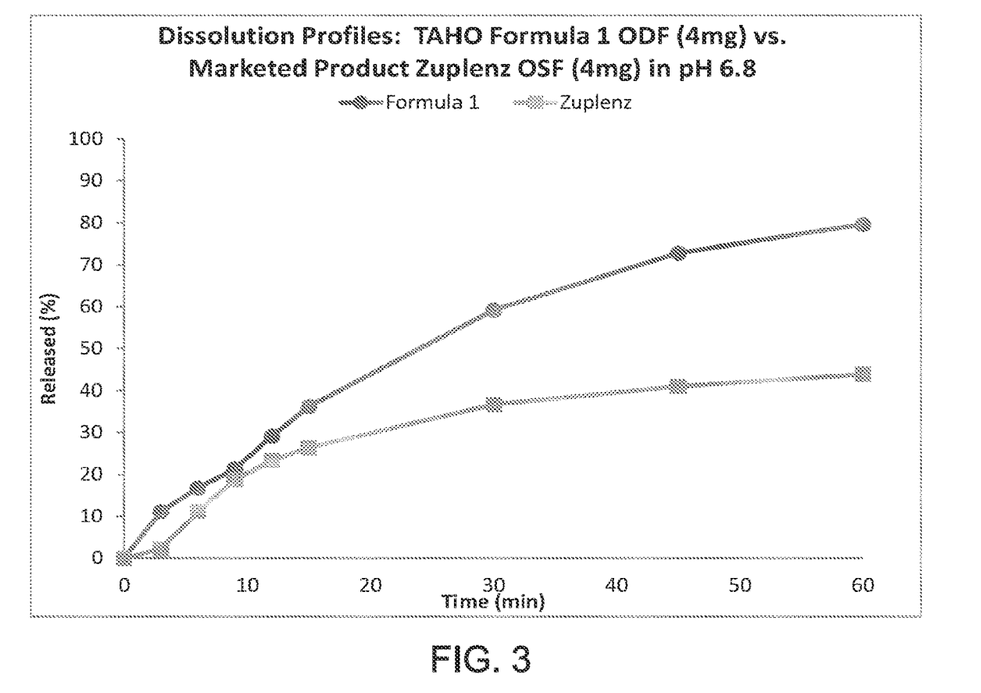
FIG. 3 is a comparison of dissolution profiles of marketed Zuplenz 4 mg ondansetron OSF against formulation 1 of 4 mg ondansetron ODF of the present invention, both dissolved using a dissolution medium at pH 6.8.
Figure 4:
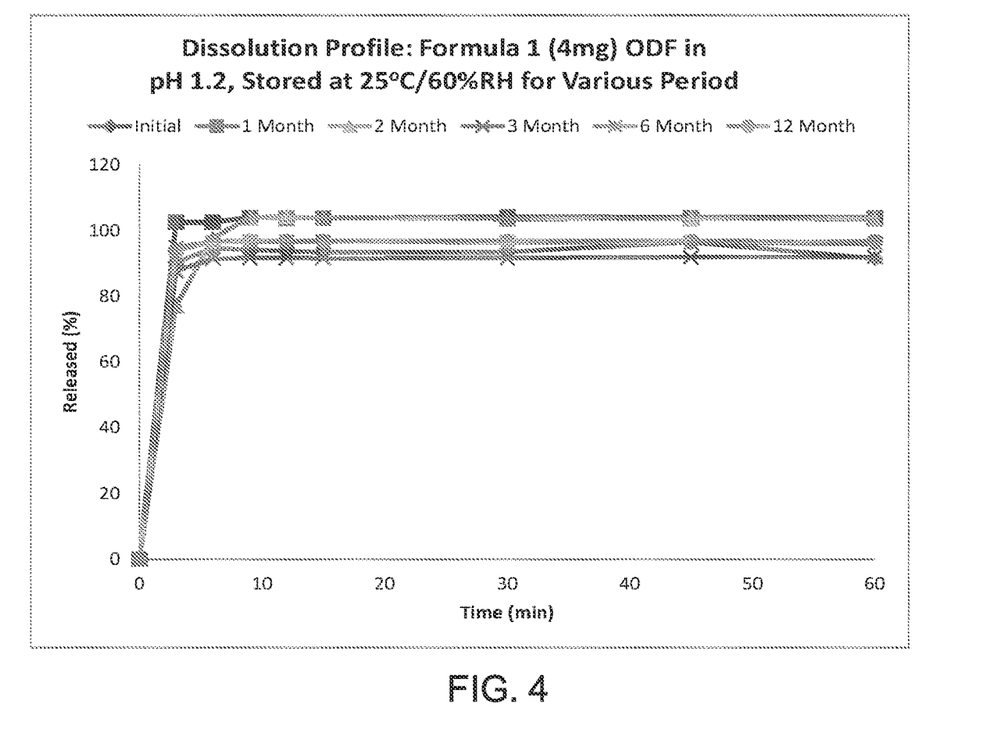
FIG. 4 illustrates stability of formulation 1 of the ODFs of the present invention by comparing dissolution profiles of the ODF stored at 25 degrees Celsius and 60% RH for 12 months and dissolved using a dissolution medium at pH 1.2.
Figure 5:
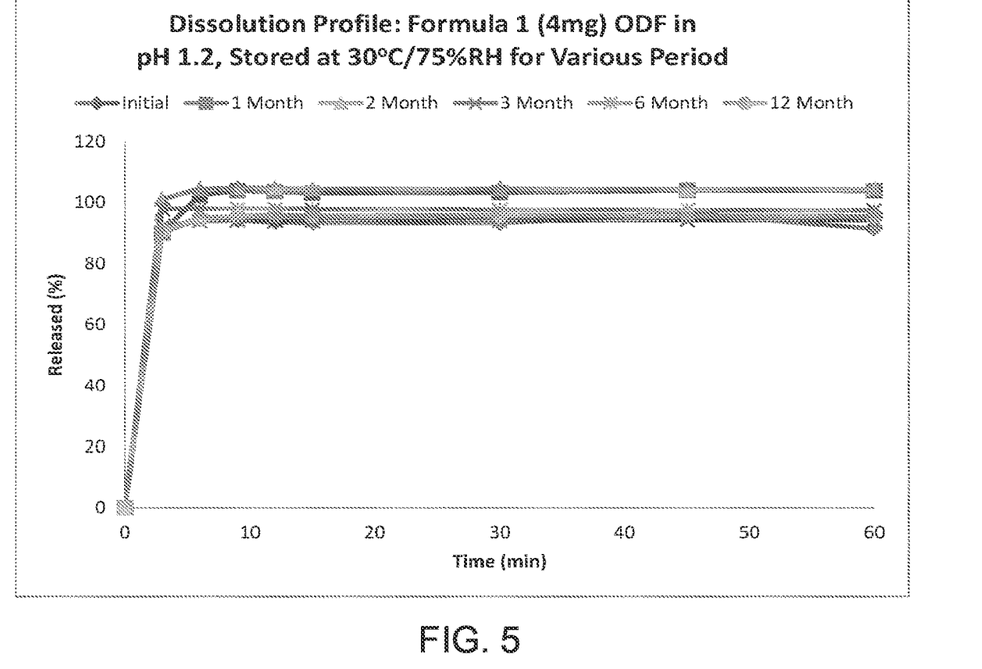
FIG. 5 illustrates stability of formulation 1 of the ODFs of the present invention by comparing dissolution profiles of the ODF stored at 30 degrees Celsius and 75% RH for 12 months and dissolved using a dissolution medium at pH 1.2.
Figure 6:
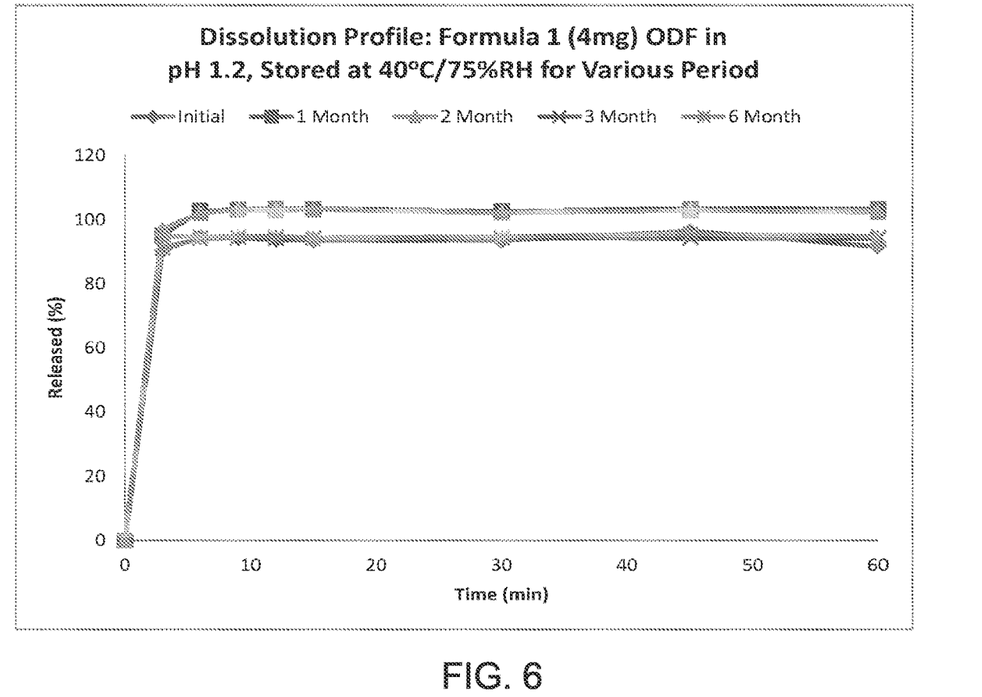
FIG. 6 illustrates stability of formulation 1 of the ODFs of the present invention by comparing dissolution profiles of the ODF stored at 40 degrees Celsius and 75% RH for 6 months and dissolved using a dissolution medium at pH 1.2.
Figure 7:
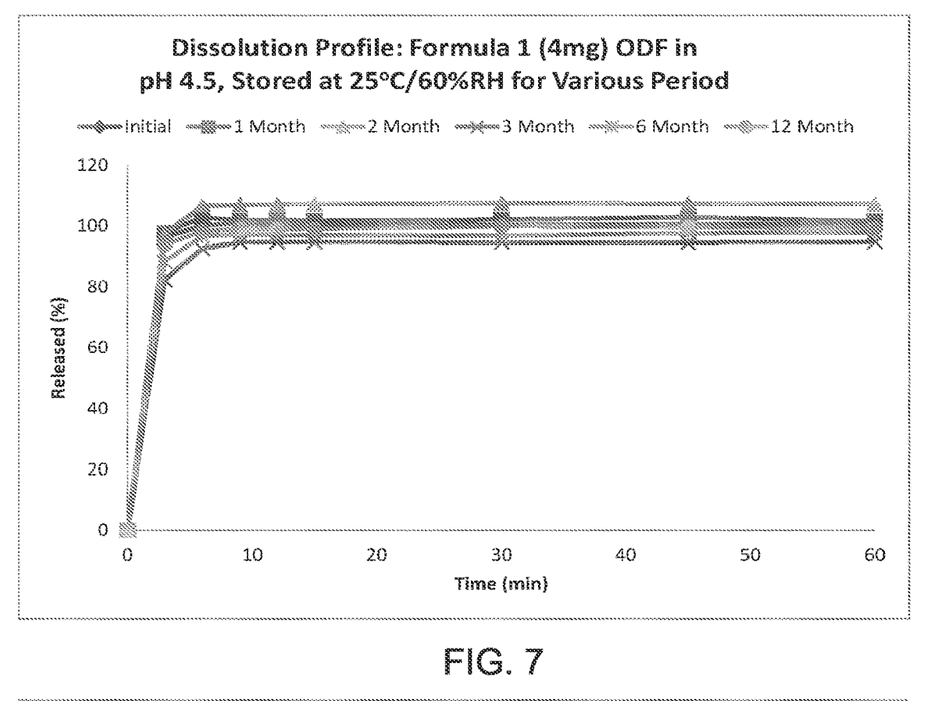
FIG. 7 illustrates stability of formulation 1 of the ODFs of the present invention by comparing dissolution profiles of the ODF stored at 25 degrees Celsius and 60% RH for 12 months and dissolved using a dissolution medium at pH 4.5.
Figure 8:
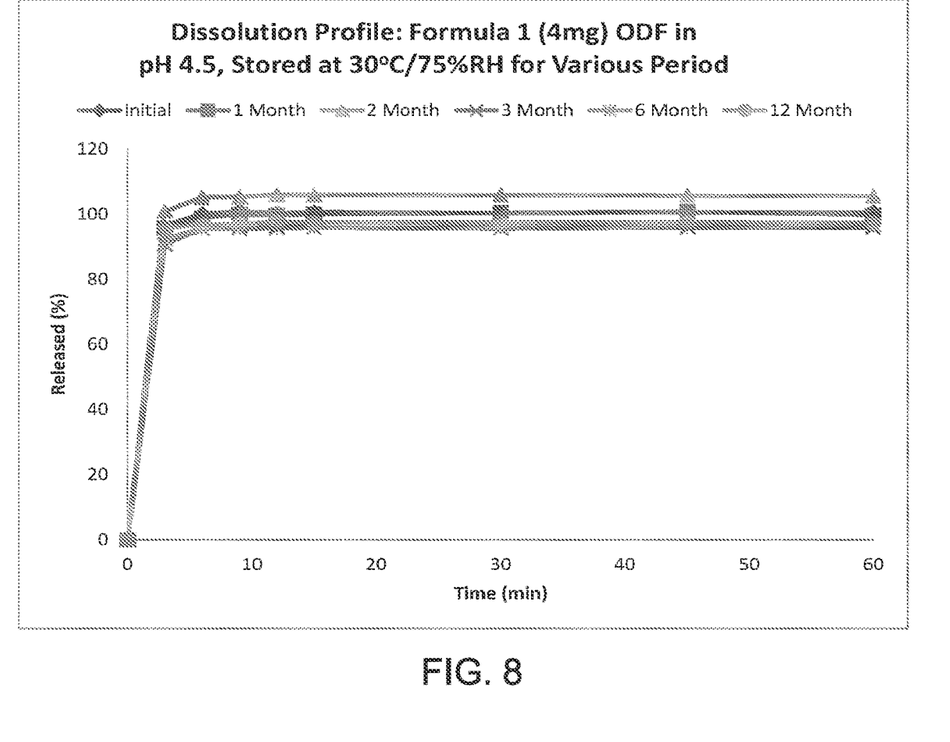
FIG. 8 illustrates stability of formulation 1 of the ODFs of the present invention by comparing dissolution profiles of the ODF stored at 30 degrees Celsius and 75% RH for 12 months and dissolved using a dissolution medium at pH 4.5.
Figure 9:
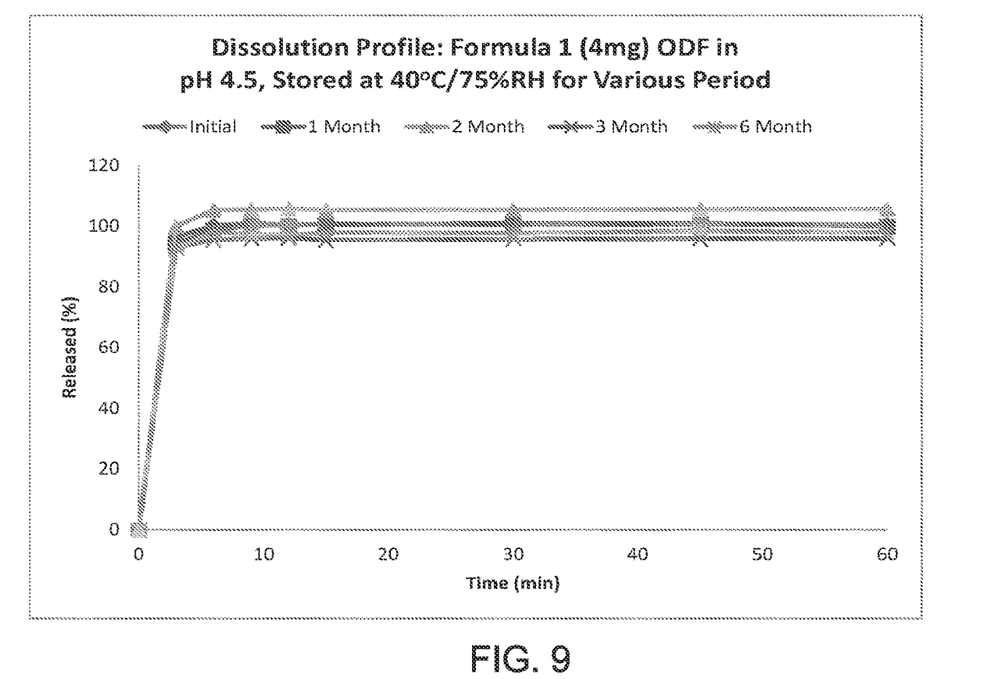
FIG. 9 illustrates stability of formulation 1 of the ODFs of the present invention by comparing dissolution profiles of the ODF stored at 40 degrees Celsius 75% RH for 6 months and dissolved using a dissolution medium at pH 4.5.
Figure 10:
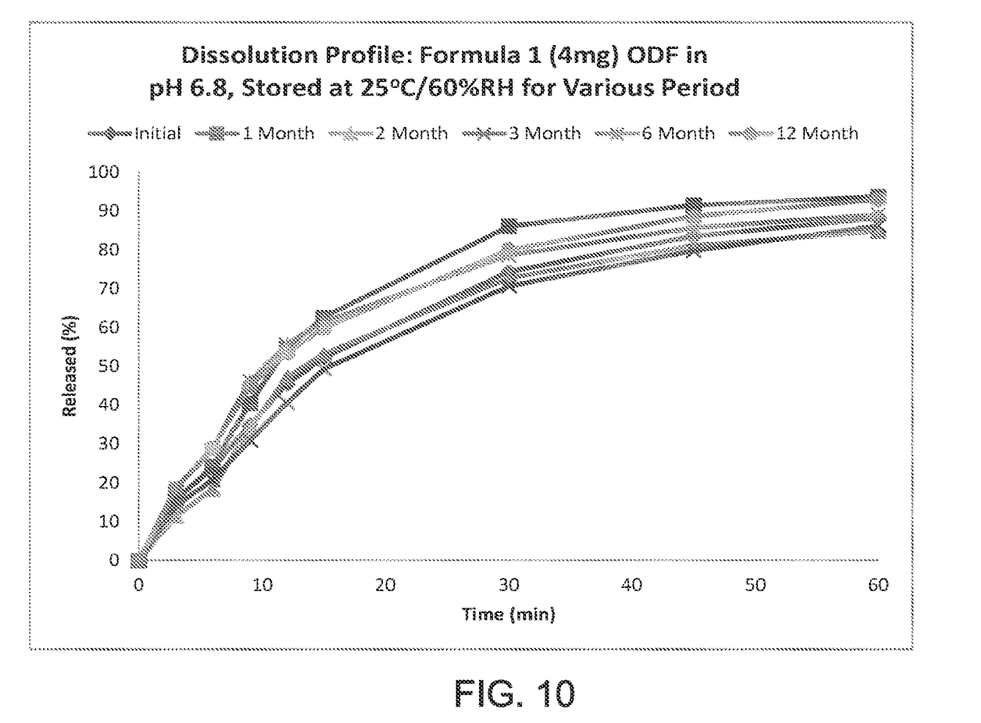
FIG. 10 illustrates stability of formulation 1 of the ODFs of the present invention by comparing dissolution profiles of the ODF stored at 25 degrees Celsius and 60% RH for 12 months and dissolved using a dissolution medium at pH 6.8.
Figure 11:
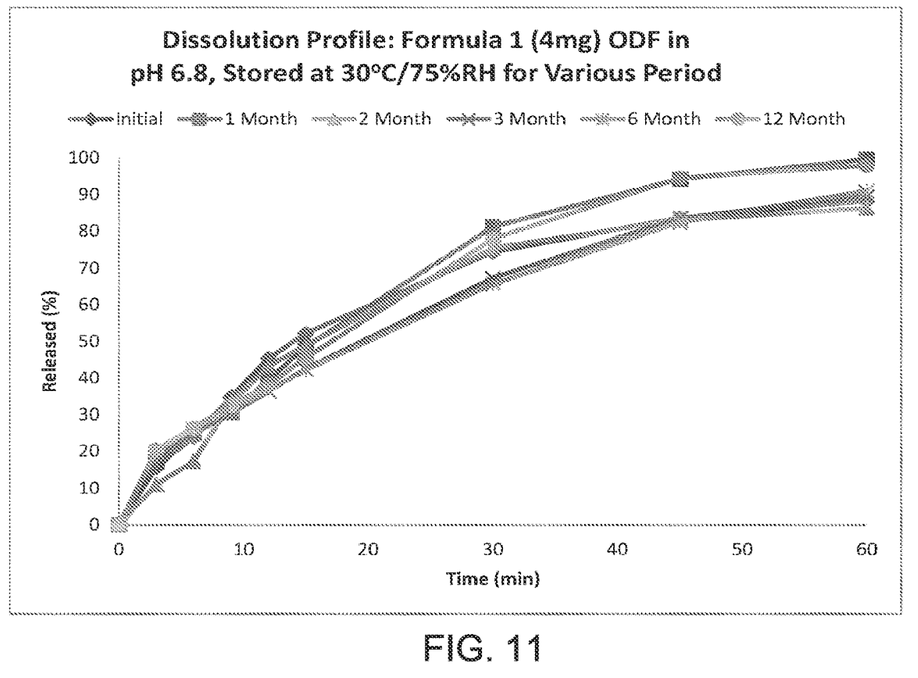
FIG. 11 illustrates stability of formulation 1 of the ODFs of the present invention by comparing dissolution profiles of the ODF stored at 30 degrees Celsius and 75% RH for 12 months and dissolved using a dissolution medium at pH 6.8.
Figure 12:
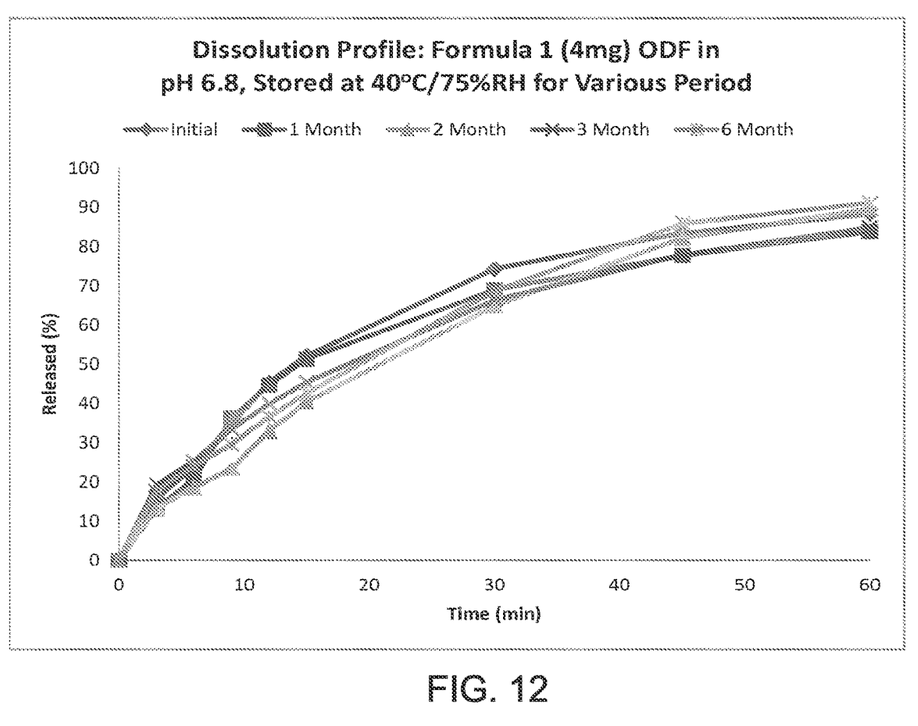
FIG. 12 illustrates stability of formulation 1 of the ODFs of the present invention by comparing dissolution profiles of the ODF stored at 40 degrees Celsius and 75% RH for 6 months and dissolved using a dissolution medium at pH 6.8.

Moreover, FIGS. 1, 2 and 3 illustrate that formula 1 of the ODF of the present invention shown in table 2A has faster dissolution times than Zuplenz® 4 mg ondansetron oral soluble film (OSF) manufactured by Monsol Rx LLC and distributed by Galena Biopharma, Inc. (It should be noted that OSF is the specific designation used by MonoSol for Zuplenz OSF as well as the approved FDA label identification for Zuplenz OSF; however, since they both describe an orally dissolving film, ODF and OSF should be regarded as interchangeable terms.) Specifically, referring to FIGS. 1 and 2, the ODF of the present invention achieves complete dissolution within 10 minutes whereas the Zuplenz 4 mg ondansetron OSF does not achieve complete dissolution even at the 30 minute mark. Importantly, dissolution time is one of the most crucial properties of an ODF since faster dissolution allows for quicker absorption of the ondansetron and, hence, allows for quicker symptom relief. Therefore, in addition to short disintegration time, the short dissolution time of the ODF of the present invention also contributes to the fast acting aspect of the ODF.

In addition, the ODF of the present invention is also stable over time without use of functional excipients such as stability agents. Specifically, FIGS. 4-13 and table 5 show that formula 1 of the ODF of the present invention listed in table 2A is just as stable if not more stable as other ondansetron products currently being marketed such as Zuplenz 4 mg ondansetron OSF even without use of stability agents. Referring to the data shown in FIG. 13 and tables 4 and 5, formulation 1 of the ODF of the present invention achieves superior stability when compared to marketed Zuplenz 4 mg ondansetron OSF. Specifically, while FIG. 13 and table 5 show that dissolution of formulation 1 of the ODF of the present invention do not vary appreciably, they show that the dissolution of the marketed Zuplenz 4 mg ondansetron OSF vary considerably, especially in the 10 to 20 minutes range where the different dissolution profiles can differ by nearly 20%.

Furthermore, formulation 1 of the ODF of the present invention is able to withstand greater tension force than the marketed Zuplenz 4 mg ondansetron OSF as shown in table 6. This can be said for various other formulations of the ODF of the present invention shown in tables 2A and 2B. This suggests that the ODF of the present invention is better able to withstand handling. In addition to having fast disintegration and dissolution times, stability and strength, the ODF of the present invention can be produced with an even API distribution and a smooth appearance substantially free of gas bubbles.

In an embodiment, the ODF of the present invention comprises ondansetron or a pharmaceutical acceptable salt thereof in an amount of about 2 to 24 mg, a water soluble excipient in an amount of about 10 to 55% by weight of the ODF and a first set of one or more hydrophilic film forming polymers comprising at least about 8%, at least about 15%, at least about 20%, at least about 30%, at least about 50% or at least about 65% by weight of the ODF, wherein the one or more hydrophilic film forming polymers is each characterized by having molecular weight of about 5000 to 50000 Da, about 10000 to 50000 Da, about 20000 to 50000 Da or about 30000 to 50000 Da and having viscosities of between about 3 to 50 cps, about 5 to 50 cps or about 6 to 50 cps. More preferably, the hydrophilic film forming polymers is each characterized by having molecular weight of about 30000 to 50000 Da and viscosities of about 3 to 10 cps.

According to another embodiment of the present invention, the ODF may further comprise a second set of one or more hydrophilic film forming polymers each with molecular weight of about 50000 to 700000 Da and viscosity of about 50 to 2500 cps, wherein said first set of hydrophilic film forming polymers may be mixed with said second set of hydrophilic film forming polymer in a ratio of at least about 0.1:1, at least about 0.3:1, at least about 0.5:1, at least about 0.75:1, at least about 1:1, at least about 3:1 and at least about 7:1 ratio by weight. More preferably, the molecular weight of the one or more second set of hydrophilic film forming polymers is about 500000 to 60000 Da and viscosity of about 10-20 cps with ratio of the first set of hydrophilic film form polymers to the second set of hydrophilic film forming polymers at about 0.5:1.

According to yet another embodiment of the present invention, the ODF may comprise only the first or second set of one or more hydrophilic film forming polymers.

The present invention also provides a method for preparing a fast acting ODF. The method preferably comprises the step of dissolving in water a water-soluble excipient in an amount of about 10 to 55% by weight of the resulting ODF product with a pharmaceutically acceptable amount of ondansetron or a salt thereof. Next, a first set of one or more hydrophilic film forming polymer comprising in total of at least about 8%, at least about 15%, at least about 20%, at least about 30%, at least about 50% or at least about 65% by weight of the ODF is preferably also dissolved in the solution to form a viscous solution, wherein the one or more hydrophilic film forming polymers is each characterized by having a molecular weight of about 5000 to 50000 Da, about 10000 to 50000 Da, about 20000 to 50000 Da or about 30000 to 50000 Da and having viscosities of between about 3 to 50 cps, about 5 to 50 cps or about 6 to 50 cps. More preferably, the hydrophilic film forming polymers is each characterized by having molecular weight of about 30000 to 50000 Da and viscosities of about 3 to 10 cps.

In another embodiment, the method may further comprise the step of mixing a second set of one or more film forming polymers characterized by having a molecular weight of about 50000 to 700000 Da and viscosity of about 50 to 2500 cps, wherein said second set of hydrophilic film forming polymers may be mixed with another hydrophilic film forming polymer in a ratio of at least about 0.1:1, at least about 0.3:1, at least about 0.5:1, at least about 0.75:1, at least about 1:1, at least about 3:1 and at least about 7:1 ratio by weight. More preferably, the molecular weight of the one or more second set of hydrophilic film forming polymers is about 500000 Da to 60000 Da and viscosity of about 10-20 cps with the ratio of the first set of hydrophilic film form polymers to the second set of hydrophilic film forming polymers at about 0.5:1.

According to yet another embodiment of the present invention, the ODF may comprise only the first or second set of one or more hydrophilic film forming polymers.

Preferably, the solution is kept under rotation until the hydrophilic film forming polymers have completely dissolved and a homogeneous blend has been obtained. The solution is prepared in such a way as to form a pre-casting blend with a measured viscosity of about 2000 to 10000 cps. More preferably, the pre-casting blend may be carefully adjusted to yield a viscosity of about 3000 to 5000 cps. Preferably, viscosity of the pre-casting blend should not be below about 1500 cps. The viscous solution is preferably left overnight to eliminate gas bubbles.

Next, the solution is transferred onto a surface of a suitable carrier material and dried to form the ODF. Examples of suitable carrier material are non-siliconized polyethylene terephthalate film, non-siliconized paper, polyethylene-impregnated kraft paper or non-siliconized polyethylene film. Transfer of the solution onto the carrier material can be performed using any conventional film coating equipment. Drying of the film may preferably be carried out in a high-temperature air-bath using a drying oven, drying tunnel, vacuum drier, or any other suitable drying equipment known to those skilled in the art. For example, the film may be dried in an oven at about 8G° C. over a period of about 20 minutes so as to form the orally administrable film of desired thickness and may then be cut into desired size.

In yet another embodiment, method of the present invention may further comprise the step of adding other ingredients such as one or more flavoring agent, sweetening agent and coloring agent to be dissolved or mixed with the pharmacologically active agent, hydrophilic film forming polymers and water soluble excipients in the method for preparing the film.

The present invention also provides a method for treating various medical conditions such as medical conditions using ODF of the present invention. For example, the fast acting ODF of the present invention with ondansetron can be used to treat, prevent, or alleviate the occurrence of emesis, nausea and/or vomiting. The nausea and/or vomiting may be associated with medical treatments such as but not limited to chemotherapy and/or radiation or associated with certain conditions such as but not limited to pregnancy, motion sickness, car sickness or sea sickness. The fast acting ODF is administered by placing it in the oral cavity of the subject, such as on or beneath the tongue and allowing it to disintegrate and then dissolute extensively in bodily fluid so as to achieve gastrointestinal absorption of the active ingredient. The ODF may be administered to a subject in a fed state or a fasted state with little effect on dissolution rate. The fast acting ODF may also be administered with or without water. According to some embodiments, more than one ODF may be administered sequentially, preferably by placing the fast film dosage form in the oral cavity until it disintegrates before administering the next dosage. Therefore, the ODF may be administered once daily or as frequently as twice daily or three times a day before or after receiving the chemotherapy or radiation therapy. For example, the ODF containing 4 mg of ondansetron may be administered three times a day, preferably every 4 to about 12 hours, preferably every 6 to about 10 hours, more preferably every 8 hours, for about 1 to 5 days, preferably about 1 to 2 days, after completion of chemotherapy.

In practice, the films can be used simply by removing the product from its package and placing the film in a moist environment, e.g., on or under the tongue, until it disintegrates. The films described herein can be provided in a variety of sizes, depending upon their intended use, the amount of drug loading desired, the duration of erosion, the duration of drug delivery and so forth.

The hydrophilic film forming polymer referred to above can preferably be saccharide-based or nonsaccharide-based water soluble polymer. Specific examples of saccharide-based water soluble polymer include but are not limited to alkylcelluloses, hydroxylalkylcelluloses and hydroxylalkylalkylcelluloses such as methylcellulose, hydroxylmethylcellulose, hydroxyethylcellulose, hydroxylpropylcellulose (HPC), hydroxyethylmethylcellulose, hydroxypropylmethylcellulose (HPMC) or hypromellose and hydroxybutylmethylcellulose, pullulan, carboxymethylcellulose (CMC) such as sodium CMC, and combinations thereof.

Specific examples of the non-saccharide-based water soluble polymer include but are not limited to polyacrylic acids and polyacrylic acid esters, polymethacrylic acid and polymethacrylic acid esters, polyalkylene oxides, such as polyethylene oxide, polyvinylacetates, polyvinylalcohols, polyvinylacetatephthalates (PVAP), polyvinylpyrrolidone (PVP) or povidone, polyvinyl acetate copolymers, and polycrotonic acids. In the more preferred examples of the present invention, the hydrophilic film forming polymers may include hypromellose, HPC, sodium CMC pullulan and povidone.

The pharmaceutically acceptable excipient referred to in the previous two paragraphs immediately above may preferably comprise plasticizer. Examples of the plasticizer include but are not limited to glycerin, polyethylene glycol (PEG) or Macrogol, diethylene glycol, tripropylene glycol, ethylene glycol, triethylene glycol, 1,3 butanediol and 1,4 butanediol. Other examples of the plasticizer may include but not limited to polysorbates such as polysorbate 20 (or Tween 20) and polysorbate 80. In one embodiment, the plasticizer used for formulating the film may include PEGs of various molecular weights. Preferably, examples of PEGs include PEG 6000, PEG 4000, PEG 3350, PEG 2000, PEG 1000 and PEG 400.

Examples of the flavoring agent referred to above may include, but are not limited to flavor oils such as peppermint oil, cinnamon oil, spearmint oil and oil of nutmeg, and flavor essence extracted from vanilla, cocoa, coffee and chocolate, and fruit essence obtained from apple, raspberry, cherry, pineapple and other citrus fruits such as orange, lemon and lime. Specific examples of the sweetening agent used in the present invention may include saccharine, sucrose, fructose, glucose, sucralose and mannitol. Examples of the coloring agents may include, but are not limited to Food Drug and Cosmetic (FD&C) colors such as FD&C Blue 1 Aluminum Lake, FD&C Yellow 5 Aluminum Lake, FD&C Yellow No. 6 Lake or any other pharmaceutically acceptable color additives that impart colors when added to the pharmaceutical composition. Other examples of the pharmaceutically acceptable excipients or additives commonly known to those skilled in the art may also be optionally added with the active ingredient as needed.

In the discussions of figures and tables below, all references to ODF of the present invention refer to formulation 1 of table 2A. In addition, all experiments were each carried out N=3 times as per standard laboratory practice. It should be noted that dissolution profiles can plateau slightly above or below 100% due to slight ondansetron content variations. In all cases, plateauing of the dissolution profile curves should indicate completion of dissolution.

FIGS. 4-12 and table 3 illustrate stability of the ODF of the present invention. Referring to FIG. 4-12 and table 3, the dissolution profiles show little to no change for ondansetron ODF samples at 25 degrees Celsius with 60% relative humidity, 30 degrees Celsius with 65% relative humidity and 40 degrees Celsius with 75% humidity storage conditions for up to 12 months. The dissolution is done in pH 1.2, pH 4.5 and pH 6.8 with the rotational basket method at 50 rpm. It should be noted that, according to ICH guidance Q1E, accelerated conditions at 40 degrees Celsius and 75% RH for 6 months and long term conditions at 30 degrees Celsius and 75% RH for 12 months and 25 degrees Celsius and 60% RH for 12 months suggest a shelf-life of 24 months at room temperature.

Referring to table 3, the impurity data in the table further illustrate stability of the ODF of the present invention. As show in table 3, there is little to no impurities present at end of each storage period at temperature of 25 degrees Celsius with 60% relative humidity, 30 degrees Celsius with 65% relative humidity and 40 degrees Celsius with 75% humidity for various relative retention times. Acceptable impurity level is <0.1% as defined by ICH Q1A, Q3B and Q1F.

Therefore, the ODF is stable and free of or with negligible impurities even after storing at a temperature of about 25° C. to 4G° C. and a relative humidity of 60% to 75% for up to 12 months without aid of stabilizing agents.

Figure 13:
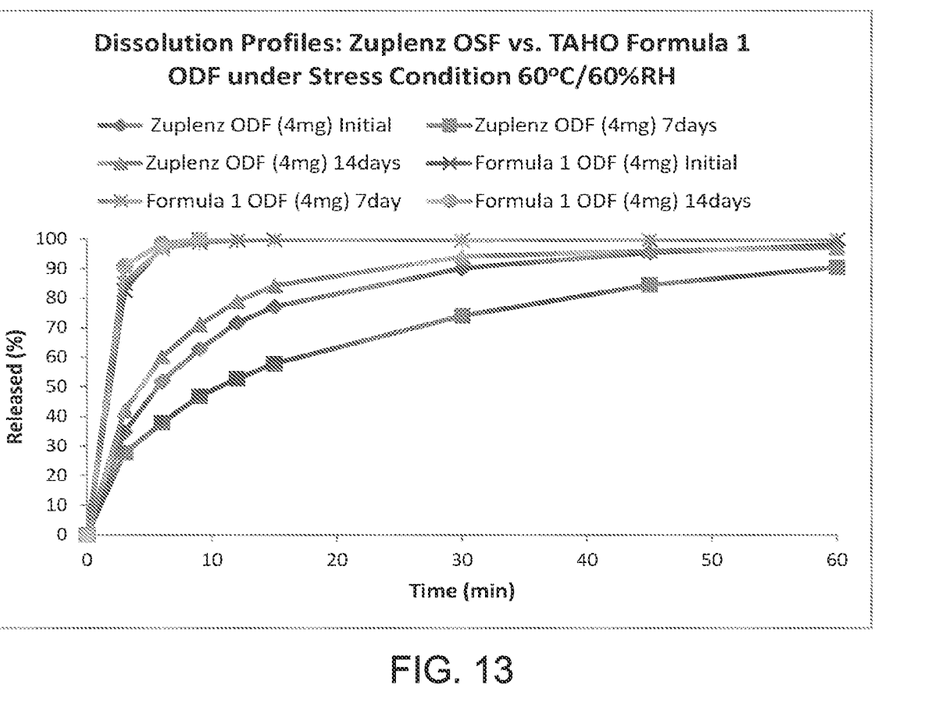
FIG. 13 compares stability of formulation 1 of the ODFs against stability of marketed Zuplenz 4 mg ondansetron OSF stressed under 60 degrees Celsius and 60% RH for 0 days, 7 days and 14 days.

FIG. 13 and tables 4 and 5 compare accelerated stability of the ODF of the present invention to marketed Zuplenz 4 mg ondansetron OSF"" The tested samples were stored in 60 degrees Celsius and 60% RH for 7 and 14 days respectively.

Referring to FIG. 13 and tables 4 and 5, dissolution data of formula 1 of the ODF of the present invention shows that the ODF is more stable compared to the marketed Zuplenz 4 mg ondansetron OSF. Specifically, dissolution data of table 4 illustrate dissolution profile of formula 1 of the ODF of the present invention does not change substantially under various storage conditions whereas there are substantial variations in dissolution profiles of the marketed Zuplenz 4 mg ondansetron OSF, as much as 20% difference between dissolution profiles between 10 to 20 minutes dissolution time range. In addition, table 4 illustrates that all samples tested contained impurities substantially below 0.1% level of acceptable impurity for various relative retention time.

Finally, referring to table 6, tension force data obtained using Tintus Olsen HIKS with method program force vs. position show that ODF of the present invention is better able to withstand tension force and, therefore, forces experienced during normal handling than Zuplenz OSF.

The features and advantages of the present invention are more fully shown by the following examples which are provided for purposes of illustration, and not to be construed as limiting the invention in any way.

Example 1: Preparation of Film Using HPMC (20000-58300 Da) and/or NaCMC (90000-700000 Da)

The process for preparing Example 1 began with dissolving 20.4 wt % of excipient PEG 6000 in water followed by dissolving 4.19 mg of ondansetron hydrochloride per unit dose in the same solution while sonication was applied to make solution 1a. Next, a coloring agent such as Blue 1 Aluminum Lake and a flavoring agent such as peppermint oil were suspended in water and homogenized at 600 rpm to form solution 2a. Solution 3a was prepared by adding 0.35 wt % sucrolase in water followed by vertexing to ensure sucrolase is well dissolved in water.

Water soluble hydrocolloids such as HPMCs of 6 cps and 15 cps in 22.85 wt % and 45.55 wt % were then mixed into solution 1a using a mixing machine operated at 800 rpm to create solution 4a. Finally, solutions 2a, 3a and 4a were then mixed together to create final mix solution.

The mixture solution was then left overnight to eliminate any gas that may exist in the solution. After degassing, viscosity of the mixture solution may be determined using a method described in connection with Example 4. Upon verifying viscosity, the mixture solution was then coated with a thickness of about 600 μm on a non-treated casting film which is then dried at 8G° C. for 20 minutes using a drying oven to form a film having thickness of about 52±2 μm. The resulting film was then cut into small pieces each having an area of about 3×2 cm$^2$ and a weight of 40±1 mg in total before packaging.

A list of exemplary various formulations that have been prepared in a similar way as example 1 are provided and shown as formulations 1, 4, 7, 8, 9, 11, 12, 13, 16, 18 and 21 in tables 2A and 2B

Example 2: Preparation of Film Using HPMC (20000-58300 Da) and Pullulan (200000-30000)

The process for preparing Example 2 began with dissolving 19.38 wt % of the excipient glycerin in water followed by dissolving 4.19 mg of ondansetron hydrochloride per unit dose in the same solution while sonication was applied to make solution 1b. Next, a coloring agent such as Blue 1 Aluminum Lake and a flavoring agent such as peppermint oil were suspended in water and homogenized at 600 rpm to form solution 2b. Further, solution 3b was prepared by adding 4.5 wt % of pullulan and 0.35 wt % sucrolase in water followed by vertexing to ensure pullulan and sucrolase were well dissolved in water.

A hydrocolloid such as HPMC of 15 cps in 65 wt % was then mixed into solution 1b using a mixing machine operated at 800 rpm to form solution 4b. A mixture solution was then prepared by mixing solutions 2b, 3b and 4b.

The mixture solution was left overnight to eliminate any bubbles that exist in the mixture solution. After degassing, the mixture was then coated with a thickness of about 600 μm on a casting film. And the mixture solution could be determined for its viscosity according to the method described in Example 4 below. The coated film was then sent to a drying oven and dried at 8G° C. for 20 minutes to form a film having a thickness of about 52±2 μm. Once the drying process was completed, the film was further cut into small pieces each having an area of about 3×2 cm$^2$ and a weight of 40±1 mg in total before packaging.

A list of exemplary formulations that can be prepared in similar way as Example 2 are provided and shown in formulations 2, 3, 5, 6, 10 and 17 of tables 2A and 2B.

Example 3: Preparation of Film Using HPMC (20000-58300 Da) and Povidone (58000-130000 Da) and/or HPC (80000 Da)

The process for preparing the ODF began by dissolving 20 wt % of water soluble excipient Tween 20 in water, followed by adding 4 mg ondansetron hydrochloride per unit dose and a further sonication to make solution 1e. Next, a coloring agent such as Yellow 5 Aluminum Lake and a flavoring agent such as Lemon were suspended in water and homogenized at 600 rpm to form solution 2c. And solution 3c was prepared by adding 25.5 wt % povidone K-30 and 0.65 wt % of sucrolase in water followed by vertexing to ensure povidone K-30 and sucrolase were well dissolved in water.

The solution 1e was further added with water soluble hydrocolloid such as HPMC of 15 cps in 42.5 wt %, and mixed by a mixing machine operated at 800 rpm to form solution 4c. Subsequently, a mixture solution was prepared by mixing the solutions 2c, 3c and 4c well.

The bubble that appears in the mixture solution was removed by degassing overnight before the bubble free mixture solution was coated with a thickness of about 600 μm on a non-treated casting film. The solution could be determined for its viscosity according to the method described in Example 4 below. The coated film was then sent to a drying oven and dried at 80° C. for 20 minutes to form a film having a thickness of about 52±2 μm. Once the drying process was completed, the film was further cut into small pieces each having an area of about 3×2 cm$^2$ and a weight of 40±1 mg in total before packaging.

A list of exemplary formulations that can be prepared in a similar way as Example 3 are provided and shown in formulations 14, 15, 19, 20 and 22 of tables 2A and 2B.

Example 4: Preparation of Viscometer and Viscosity Measurement

The viscosity of the mixture solution was determined by the use of a Brookfield Viscometer with a model type of Brookfield DV-II+Pro (Brookfield Engineering Laboratories, Inc.). Viscosity is a measure of the ratio of shearing stress to rate of shear and illustrated in the equation below.

$$\text{Shear stress (dynes)/rate of shear (cm/sec)=Poises}$$

The Brookfield Viscometer measures viscosity by measuring the force required to rotate a spindle in a fluid. Therefore, the viscosity can be read directly on the DV-II+Pro.

Preparation of Viscometer

The set-up of the viscometer was checked to ensure it is leveled. The level was adjusted using the three leveling screws on the base so that the bubble level on top of the viscometer is centered within the circle. On the other hand, a S64 spindle was prepared by cleaning with non-abrasive cloth and alcohol solvent.

Viscosity Measurement

The viscosity measure was carried with the following procedures:
1) Turn the power switch (located on the rear panel) to the ON position.
2) Press any button when the message "remove spindle" appears in the display screen.
3) Rinse S64 spindle thoroughly with deionized and distilled water.
4) The spindle was attached to the viscometer by screwing in an anti-clockwise direction.
5) spindle selection:
   i) Press "select spindle";
   ii) Select "S64" spindle using UP/DOWN button.
6) speed selection & setting:
   i) Press "set speed";
   ii) Select 30 rpm or appropriate speed for other samples using UP/DOWN button.
7) press "motor on/off" to initiate the spindle.
8) insert and center the spindle in the test sample until the fluid's level is at the immersion groove on the spindle's shaft.
9) viscosity measurement:
   i) when the viscosity reading is taken, ensure that the % reading in the screen display is above 50%;
   ii) record the viscosity reading when it remains constant.

A list of viscosity readings corresponding to some of the exemplary formulations as described in examples 1-3 is provided and shown in tables 1A and 1B.

It is noted that several measurements were taken at different areas and with different settings of the viscometer for each of the formulations. Therefore, the viscosity readings were provided in a range of values. For example, the viscosity readings taken for Formulation 1 generally falls within a range of 2500 to 3000 cps. Once the viscosity measurement is completed, the motor is turned off by switching the MOTOR ON/OFF switch. The spindle was removed for cleaning with alcohol solvent and Fischer wipes.

It can be appreciated by those skilled in the art that changes could be made to the examples described above without departing from the broad inventive concept thereof. It is understood, therefore, that this invention is not limited to the particular examples disclosed, but it is intended to cover modifications within the spirit and scope of the present invention as defined by the appended claims.

It is to be understood that both the foregoing general description and the following detailed description are exemplary and explanatory only and are not restrictive of the invention, as claimed.

These and other changes can be made to the technology in light of the detailed description. In general, the terms used in the following disclosure should not be construed to limit the technology to the specific embodiments disclosed in the specification, unless the above detailed description explicitly defines such terms. Accordingly, the actual scope of the technology encompasses the disclosed embodiments and all equivalent ways of practicing or implementing the technology.

We claim:

1. An orally disintegrating film, comprising:
    ondansetron or a pharmaceutical acceptable salt thereof in an amount of about 2 to about 24 mg;
    a first hydrophilic film forming polymer in a total amount of from about 15% to about 50% by weight of said film, wherein said first hydrophilic film forming polymer is characterized by having a molecular weight of about 5000 Da to about 50000 Da and viscosity of about 3 cps or about 6 cps; and
    a second hydrophilic film forming polymer having a molecular weight between about 50000 Da to about 60000 Da and viscosity of about 15 cps,
    wherein said first hydrophilic film forming polymer is mixed with said second hydrophilic film forming polymer in a ratio from about 0.3:1 to about 7:1; and
    the orally disintegrating film disintegrates within about 30 seconds in about 20 cc of water at about 37 degrees Celsius and lightly shaken.

2. The orally disintegrating film of claim 1, comprising a mixture of said first hydrophilic film forming polymer to said second hydrophilic film forming polymer in a ratio from about 0.5:1 to about 7:1.

3. The orally disintegrating film of claim 1, comprising said first hydrophilic film forming polymer in a total amount of from about 20% to about 50% by weight of said film.

4. The orally disintegrating film of claim 1, wherein said first hydrophilic film forming polymer comprises at least one member selected from hydroxylpropylmethylcellulose (HPMC), hydroxypropylcellulose, carboxymethylcellulose, polysaccharide polymer and povidone.

5. The orally disintegrating film of claim 1, wherein said second hydrophilic film forming polymer comprises at least one member selected from hydroxylpropylmethylcellulose (HPMC), hydroxypropylcellulose, carboxymethylcellulose, polysaccharide polymer and povidone.

6. The orally disintegrating film of claim 1, further comprising a water-soluble excipient.

7. The orally disintegrating film of claim 1, wherein the water-soluble excipient comprises polyethylene glycol (PEG) in an amount of about 10% to about 30% by weight of said film.

8. The orally disintegrating film of claim 1, further comprising one or more flavoring agent, sweetening agent and/or coloring agent.

9. An orally administered film characterized by a pre-drying solution blend with a measured viscosity of about 2000 to about 10000 cps, wherein the pre-drying solution blend comprises:
    an active pharmaceutical ingredient comprising ondansetron or pharmaceutical acceptable salt thereof in an amount of about 2 to about 24 mg;
    a first hydrophilic film forming polymer comprising hydroxylpropylmethylcellulose (HPMC) in an amount of from about 15% to about 50% by weight of the film, said first hydrophilic film forming polymer is characterized by having a molecular weight of about 5000 Da to about 50000 Da and viscosity of about 3 cps or about 6 cps;
    a second hydrophilic film forming polymer comprising HPMC characterized by having a molecular weight of between about 50000 Da to about 60000 Da and viscosity of about 15 cps, wherein said first hydrophilic film forming polymer is mixed with said second film forming polymer in a ratio from about 0.3:1 to about 7:1.

10. The orally administered film of claim 9, comprising a mixture of said first hydrophilic film forming polymers to said second hydrophilic film forming polymers in a ratio from about 0.5:1 to about 7:1.

11. The orally administered film of claim 9, comprising said first hydrophilic film forming polymer in an amount of from about 20% to about 50% by weight of said film.

12. The orally administered film of claim 9, further comprising one or more flavoring agent, sweetening agent and/or coloring agent.

* * * * *